United States Patent [19]
Kim et al.

[11] Patent Number: 5,304,295
[45] Date of Patent: Apr. 19, 1994

[54] HIGH MOLECULAR HUMIDITY SENSOR AND MANUFACTURING METHOD THEREOF BY ELECTROCHEMICAL METHOD

[75] Inventors: Chung Y. Kim; Hee-Woo Rhee; Inseok Hwang; Jai K. Kim, all of Seoul, Rep. of Korea

[73] Assignee: Goldstar Co., Ltd., Seoul, Rep. of Korea

[21] Appl. No.: 738,791

[22] Filed: Jul. 31, 1991

[30] Foreign Application Priority Data

Jul. 27, 1990 [KR] Rep. of Korea ............... 11492/1990

Related U.S. Application Data

[62] Division of Ser. No. 644,304, Jan. 19, 1991, Pat. No. 5,122,237.

[51] Int. Cl.⁵ ............................................. G01N 27/26
[52] U.S. Cl. .................................. 204/430; 204/434; 205/317
[58] Field of Search ................. 204/418, 430, 434; 205/317

[56] References Cited

U.S. PATENT DOCUMENTS

4,582,575   4/1986   Warren et al. ................. 204/59 R

FOREIGN PATENT DOCUMENTS

128478   6/1986   Japan.
124755   5/1989   Japan.

*Primary Examiner*—John Niebling
*Assistant Examiner*—Kishor Mayekar
*Attorney, Agent, or Firm*—Fliesler, Dubb, Meyer & Lovejoy

[57] ABSTRACT

A high molecular humidity sensor in which polypyrrole being of conductive high molecule is electrochemically polymerized and then reduced whereby ionic conductive property is given go that humidity sensibility becomes excellent. The sensor is a structure in which polypyrrole doped with dodecylsulfate anion $DS^-$ is stuck in film form on the surface of a fine electrode, and cations $Na^+$, $K^+$ are permeated to said polypyrrole whereby salt is formed and humidity sensibility is exhibited in the region of $10^4$–$10^6 \Omega$, and humidity sensing speed becomes within several tens of seconds to several minutes.

5 Claims, 2 Drawing Sheets

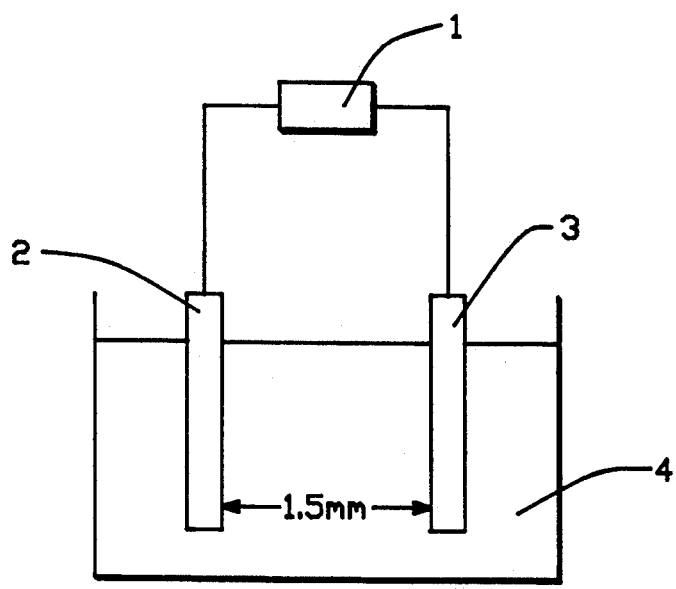
FIG.—1
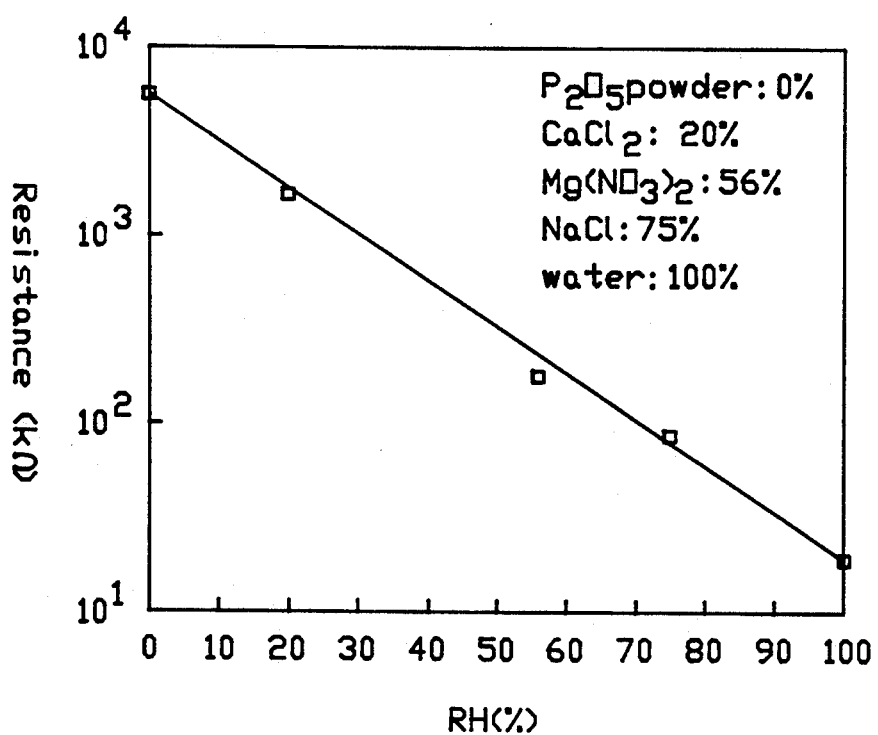
FIG.—3

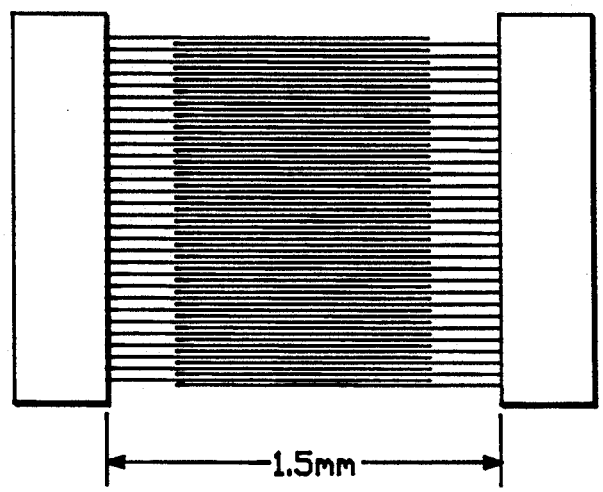
FIG.—2A
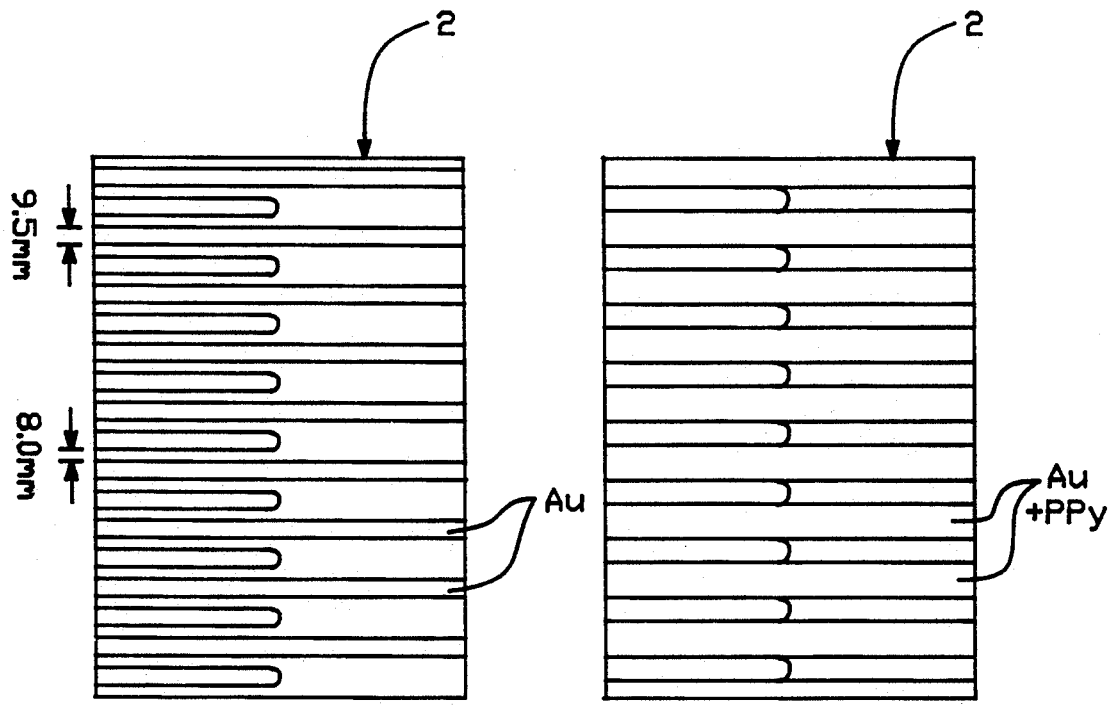
FIG.—2B  FIG.—2C

HIGH MOLECULAR HUMIDITY SENSOR AND MANUFACTURING METHOD THEREOF BY ELECTROCHEMICAL METHOD

This application is a divisional of U.S. application Ser. No. 07/644,304, filed Jan. 22, 1991, entitled HIGH MOLECULAR HUMIDITY SENSOR AND MANUFACTURING METHOD THEREOF BY ELECTROCHEMICAL METHOD, now U.S. Pat. No. 5,122,237.

BACKGROUND OF THE INVENTION

The present invention relates to a high molecular sensor and manufacturing method thereof in which polypyrrole which is a conductive high molecule is electrochemically polymerized and then reduced and thereby ionic conductivity is given so that humidity sensibility is made to be excellent.

High molecules having conjugated structures exhibit an electric conductivity essentially by doping and include polyacetylene, polyparaphenylene, polyaniline, polyacene, polypyrrole, polythiophene, and polyfuran. These conductive high molecules are used for pH sensors, pressure sensors, sulphuric acid concentration sensors, oxygen and bionic sensors, and glucose sensors and the like. Examples of such sensors are alcohol and gas sensors as well as humidity sensors. High molecules used for humidity sensors (Japanese laid-open patent publication nos. 88-133050, 88-122758, 85-201244) are polyfuran, polythiophene, polyphyrrole, heterocyclic and compounds of their derivatives. In those publications, a simple structure of glass coated with indium tin oxide (ITO) was used for an electrode of the sensor, and a separate reducing process for improving ionic conductivity was not executed. In those examples, since there is a limitation in humidity sensing speed and humidity measuring range, post-processing was required for improving the precisely-made sensor structure and ionic conductivity.

Polypyrrole, polythiophene, polyfuran and the like which are a kind of heterocyclic compound are electrochemically polymerized, and at the same time, a doping occurs to thereby produce electric conductivity. Therefore, the electric conduction operated in complex. Since the ionic conductivity produced by a non-crystalloid within the high molecule is weaker than electronic conductivity, the conductivity is substantially electronic conductivity.

SUMMARY OF THE INVENTION

An object of the present invention is to provide a high molecular humidity sensor which is excellent in humidity sensibility and humidity sensing speed.

The polypyrrole used in the present invention is among the heterocyclic high molecules that electrochemically polymerization. A polymer of the film type is formed in organic solvent such as aqueous solution and acetonitrile with a conductivity of more than 100 S/cm. Polypyrrole is good in chemical, thermal and atmospheric stability, and has electrochemical properties and physical properties that are different in accordance with the kind of pyrrole derivatives, copolymer or anion dopant.

The sensor according to the present invention is characterized in that polypyrrole doped with dodecylsulfate anion DS$^-$ in film form is coated on the fine electrode surface and cations Na$^+$, K$^+$ are permeated into the polypyrrole whereby salt is formed and humidity sensibility appears in the region of $10^4$ to $10^6$ $\Omega$ and humidity sensing speed is within several tens of seconds to several minutes.

The method of manufacturing the sensor is characterized in that the polypyrrole which is a conductive high molecule is electrochemically polymerized and thereafter reduced to produce ionic conductivity.

BRIEF DESCRIPTION OF THE DRAWINGS

FIG. 1 is a schematic structural diagram of electric polymerizing reaction bath.

FIG. 2A to FIG. 2C are diagrams illustrating electrode structure and manufacturing process of high molecular sensor, in which FIG. 2A is an enlarged diagram of a photomask used in photolithography, FIG. 2B is a diagram showing an electrode structure before polymerizing the polypyrrole, and FIG. 2C is a diagram showing an electrode structure after polymerizing the polypyrrole.

FIG. 3 is a graph of the humidity sensibility of a polypyrrole humidity sensor.

DESCRIPTION OF THE PREFERRED EMBODIMENTS

Hereinafter, the present invention will be described in detail with reference to the accompanying drawings.

FIG. 1 is a schematic diagram of an electric polymerizing reaction bath, wherein reference number 1 is a direct current-voltage source, number 2 is an operating electrode, and numeral 3 is the opposite electrode. An electrode which is designed and manufactured by photolithographic methods is used for the operating electrode. Reference number 4 is an electrolyte, which is TBADS/ACN or NaDS/H$_2$O group included with pyrrole which is a monomer upon polymerizing, in aqueous solution group including a small cation such as Na$^+$ and K$^+$ upon reducing.

FIGS. 2A to 2C are diagrams showing the electrode structure of high molecular sensor, in which FIG. 2A is a magnified photograph of the photomask structure using a photolithographic method, FIG. 2B is an enlarged photograph showing the electrode arrangement before polymerization of polypyrrole, and FIG. 2C is an enlarged photograph of the electrode arrangement after polymerization of polypyrrole. While the polymerization proceeded, the polypyrrole of dark color of FIG. 2C was grown to the brightly viewed region with the gold electrode of FIG. 2B around it.

FIG. 3 is a graph of the humidity sensibility of the polypyrrole sensor (25° C.) which used the TBADS/ACN group for the electrolyte for polymerizing and the KClO$_4$/water group for reducing.

In manufacturing the high molecular humidity sensor according to the present invention, anhydrous calcium chloride CaCl$_2$ was added to monomer pyrrole (Aldrich 90%) primarily for drying and then calcium hydride CaH$_2$ was added again and distilled under reduced pressure and refined. Thereafter the refined pyrrole was polymerized. When the pyrrole is polymerized and while the polymerizing reaction is taking place, simultaneously a radical intermediate is formed. Since the radical intermediate is influenced according to the nucleophilic degree of the electrolyte and solvent, careful attention is given to selecting the electrolyte. In the present invention, tetrabutylammonium dodecylsulfate TBADS (Korean Patent Application No. 18889, filed Dec. 19, 1989) synthesized by the inventors of this application is used for the electrolyte with sodium dodecylsulfate NaDS or acetonitrile which is a nonprotonic solvent. When the pyrrole is electrochemically polymerized in the reaction bath of FIG. 1 by using electrolyte of the NaDS or TABDS group, dodecylsulfate ion $DS^-$ is doped whereby electric conductivity is exhibited. On the other hand, even if this pyrrole is reduced for a long time (24 hours) by a voltage ($-2.5$ V) of reverse polarity during the polymerizing time in aqueous solution group such as NaDS/water, large $DS^-$ cannot get out of the film, instead, relatively smaller cations get into the film and gradually become electrically neutral. This result was confirmed by EDS/EPMA (Energy dispersive X-ray spectrometer/electronprobe microanalyzor). If the film is not extremely thin, complete electric neutrality is difficult to obtain, and under these conditions, the conduction mechanism of polypyrrole is caused by electronic conduction as well as ionic conduction.

The fine electrode of a high molecular humidity sensor used in the present invention was manufactured on a glass or alumina base plate by photolithographic method.

Tungsten was deposited as a surface film on the base plate by sputtering method, and nickel was deposited thereon by thermal evaporation. Selection of the base plate and coating of tungsten and nickel and the like provide for the durability of the sensor electrode. Positive photoresist was coated thereon again and then an infrared ray was permeated through the photomask designed as in the FIG. 2A electrode structure whereby an image was formed. Then, gold plating was deposited on the portion etched to form the designed structure and thereafter positive photoresist, nickel and tungsten were etched in turn to complete the manufacture of fine electrode. The structure of the fine electrode forms a two comb teeth pattern of electrodes that are alternately arranged beside one another with an interval between them of 7.8–9.5 μm. The electrode structure was designed so as to have as small an interval as possible to make the resistance of the high molecular sensor to be reduced toward the measuring region and to make the electrostatic capacity larger so that the humidity sensibility is maximized. The fine electrode was placed as the positive (+) electrode in the electric polymerizing reaction bath of FIG. 1 and when the legs of polypyrrole were formed between the intervals of the fine electrode, then the polymerization was stopped. The thickness of polymerized polypyrrole was adjusted by controlling the electric current (1–5 mA) and/or the polymerizing time (5–15 seconds). Next, the electrolytic solution was changed to an aqueous solution including small cations and then reduced whereby the cations were permeated. At this time, the voltage ($-0.5$ to $-1.0$ V) and reducing time (3–10 minutes) are controlled, so that the reducing degree of the film, that is, the ionic conductive property was established. The humidity sensibility of the thus manufactured high molecular sensor appeared in the region of $10^4$–$10^6$ Ω, and the humidity sensing speed was also good as within several tens of seconds to several minutes.

Hereinafter, examples of the aforementioned present invention will be described in detail as follows.

EXAMPLE 1

All experiments were carried out in the one-compartment electrolytic bath (40 cc) of FIG. 1.

Fine electrode manufactured by photolithographic method was tightly placed for positive electrode (+) and platinum electrode (3×6 cm) for negative electrode (−), and the distance between them was maintained by 1.5 mm. The electrolyte TBDA was dissolved to 40 cc of acetonitrile so as to become 0.036 mol/l. The pyrrole was added with calcium chloride $CaCl_2$ and was dried primarily and was dried secondarily by calcium hydride $CaH_2$ and then was distilled in reduced pressure (22°–25° C.). Concentration of pyrrole used executed for 10 seconds by flowing current of 3 mA at 20°–25° C. In order to execute reduction, a voltage of $-0.75$ V was applied for 5 minutes in the device of FIG. 1 with electrolyte for aqueous solution of potassium perchlorate $KClO_4$.

Thus, electronic conduction was lowered and ionic conduction was relatively increased.

In FIGS. 2B and 2C, the distance between the electrodes was 7.8–9.5 μm. As can be seen from FIG. 2C, while the polymerization proceeds, polypyrrole film is formed on each electrode, and when it reaches the thickness of a predetermined degree, a leg of polypyrrole is formed at the interval between the electrodes. FIG. 3 shows the resistance change of the high molecular humidity sensor in response to the relative humidity RH % maintained with saturated aqueous solution of various salts, and the polypyrrole is in a state that it is polymerized in TBADS/ACN and then reduced in $KClO_4$/water. The relative humidity of 100% was maintained by distilled water, and relative humidity of 0% by $P_2O_5$ powder.

EXAMPLE 2

All experimental conditions were the same as in example 1 and it was reduced by aqueous solution of $NaClO_4$ as electrolyte.

EXAMPLE 3

All experimental conditions were the same as in example 1 and aqueous solution of NaDS was used as electrolyte upon polymerizing.

EXAMPLE 4

All experimental conditions were the same as in example 2 and aqueous solution of NaDS was used as electrolyte upon polymerizing.

The high molecular humidity sensor of the present invention has the advantage that the humidity sensibility and the humidity sensing speed are excellent.

I claim:

1. A sensor having a structure comprising polypyrrole doped with dodecylsulfate anion $DS^-$ formed on a surface of a fine electrode, and cations $Na^+$ or $K^+$ permeating said polypyrrole which forms an ionically conductive salt having a humidity sensibility in a region of $10^4$–$10^6$ Ω.

2. A sensor having a structure comprising a polypyrrole doped with dodecylsulfate anion $DS^-$ formed on a surface of a fine electrode and cations $Na^+$ or $K^+$ permeating said polypyrrole which forms an ionically conductive salt having a humidity sensibility in a region of $10^4$–$10^6$ Ω, said sensor formed by electric polymerizing and then reducing where, said electric polymerizing includes, placing a structure in an electrolyte polymerizing solution as a positive electrode, said electrolytic polymerizing solution formed by a monomer pyrrole in a solution including a dopant dodecylsulfate anion DS⁻ of large molecular weight, having a negative electrode in the solution, applying a direct current between the electrodes whereby polypyrrole doped with said anion DS⁻ is formed as a film on said positive electrode, said reducing includes, placing the positive electrode in an electrolytic aqueous solution containing cations Na+ or K+, having a negative electrode in the electrolytic aqueous solution, applying a reversing polarity direct current to said positive electrode and negative electrode whereby said Na+ or K+ cations permeate said polypyrrole and said salt is formed producing ionic conductivity.

3. The sensor of claim 2 wherein said polymerizing electrolytic solution is mixed with tetrabutylammonium dodecylsulfate TBADS as an anion source and acetonitrile ACN.

4. The sensor of claim 1 wherein said positive electrode is formed of a tungsten and nickel film deposited on a base plate of glass or alumina to form a comb teeth pattern of partial electrodes of longer width portions and shorter width portions which are alternately arranged.

5. The sensor of claim 4 wherein intervals between said partial electrodes are 7.8–9.5 μm.

* * * * *